US008784807B2

(12) United States Patent
Vignali et al.

(10) Patent No.: US 8,784,807 B2
(45) Date of Patent: Jul. 22, 2014

(54) METHOD OF INHIBITING REGULATORY T-CELL ACTIVITY BY ADMINISTERING AN ANTIBODY THAT INHIBITS INTERLEUKIN 35

(75) Inventors: Dario Vignali, Germantown, TN (US); Creg Workman, Memphis, TN (US); Lauren Collison, Memphis, TN (US); Kate Vignali, Germantown, TN (US)

(73) Assignee: St. Jude Children's Research Hospital, Memphis, TN (US)

( * ) Notice: Subject to any disclaimer, the term of this patent is extended or adjusted under 35 U.S.C. 154(b) by 71 days.

(21) Appl. No.: 12/441,166

(22) PCT Filed: Sep. 24, 2007

(86) PCT No.: PCT/US2007/079310
§ 371 (c)(1),
(2), (4) Date: Aug. 7, 2009

(87) PCT Pub. No.: WO2008/036973
PCT Pub. Date: Mar. 27, 2008

(65) Prior Publication Data
US 2010/0136019 A1    Jun. 3, 2010

Related U.S. Application Data

(60) Provisional application No. 60/846,434, filed on Sep. 22, 2006.

(51) Int. Cl.
*A61K 39/395* (2006.01)

(52) U.S. Cl.
USPC ........................................................ 424/130.1

(58) Field of Classification Search
None
See application file for complete search history.

(56) References Cited

U.S. PATENT DOCUMENTS

| 5,744,301 A | 4/1998 | Birkenbach et al. |
| 5,830,451 A * | 11/1998 | Devergne et al. ............ 424/85.1 |
| 2005/0214296 A1* | 9/2005 | Kastelein et al. .......... 424/145.1 |
| 2009/0220498 A1 | 9/2009 | Finotto |

FOREIGN PATENT DOCUMENTS

| EP | 0 894 854 A2 | 2/1999 |
| WO | WO 94/12519 | 6/1994 |
| WO | WO 97/13859 | 4/1997 |
| WO | WO 01/40257 | 6/2001 |
| WO | WO 2005/079848 | 9/2005 |
| WO | WO 2005/090400 | 9/2005 |
| WO | WO 2007/045389 | 4/2007 |
| WO | WO 2008/070097 A1 | 6/2008 |
| WO | WO 2011/028390 A1 | 3/2011 |
| WO | WO 2011/063198 A2 | 5/2011 |

OTHER PUBLICATIONS

Collison, L.W., et al., "The Inhibitory Cytokine IL-35 Contributes to Regulatory T-Cell Function", *Nature*, vol. 450, (Nov. 22, 2007), pp. 566-571.
Devergne, O., et al., "Epstein-Barr Virus-Induced Gene 3 and the p35 Subunit of Interleukin 12 Form a Novel Heterodimeric Hematopoietin", *Proc. Natl. Acad. Sci.*, vol. 94 (Oct. 1997), pp. 12041-12046.
Maguire Van Seventer, J., et al., "Interferon-β Differentially Regulates Expression of the IL-12 Family Members p35, p40, p19 and EB13 in Activated Human Dendritic Cells", *Journal of Neuroimmunology*, vol. 133 (2002), pp. 60-71.
Niedbala, W., et al., "IL-35 is a Novel Cytokine with Therapeutic Effects Against Collagen-Induced Arthritis Through the Expansion of Regulatory T Cells and Suppression of Th17 Cells", *Eur. J. Immunol.*, vol. 37, (2007), pp. 3021-3029.
Wirtz, S., et al., "EBV-Induced Gene 3 Transcription is Induced by TLR Signaling in Primary Dendritic Cells via NF-κB Activation", *The Journal of Immunology*, vol. 174, (2005), pp. 2814-2824.
Fecci, P.E., "Systemic Anti-CD25 Monoclonal Antibody Administration Safely Enhances Immunity in Murine Glioma without Eliminating Regulatory T Cells," *Clinical Cancer Research*, Jul. 15, 2006, vol. 12(14), pp. 4294-4305.
Furuichi, Y., et al., " Depletion of CD25+CD4+T cells (Tregs) enhances the HBV-specific CD8+ T cell response primed by DNA immunization," *World Journal of Gastroenterology*, Jun. 28, 2005, vol. 11(24), pp. 3772-3777.
U.S. Appl. No. 13/389,106, St. Jude Children's Research Hospital.
Collison, L., "Regulatory T. Cell Supression Is Potentiated by Target T Cells in a Cell Contact, IL-35- and IL-10-Dependent Manner,"*The Journal of Immunology*, 2009, vol. 182(10), pp. 6121-6128.
Phelan, J., et al., "Cutting Edge: Mechanism of Enhancement of in Vivo Cytokine Effects by Anti-Cytokine Monoclonal Antibodies," The Journal of Immunolou, 2008, vol. 180(1), pp. 44-48.
Mapara, M.Y., et al., "Tolerance and Cancer: Mechanisms of Tumor Evasion and Strategies for Breaking Tolerance," *Journal of Clinical Oncology*, Mar. 15, 2004, vol. 22(6), pp. 1136-1151.

* cited by examiner

*Primary Examiner* — Robert Landsman
(74) *Attorney, Agent, or Firm* — Alston & Bird LLP

(57) ABSTRACT

Methods for regulating T cell function in a subject, particularly regulatory T cell activity are provided. Methods of the invention include administering to a subject a therapeutically effective amount of an Interleukin 35-specific binding agent, such as an antibody or small molecule inhibitor. The invention further provides methods for enhancing the immunogenicity of a vaccine or overcoming a suppressed immune response to a vaccine in a subject, including administering to the subject a therapeutically effective amount of an IL35-specific binding agent and administering to the subject a vaccine. In one embodiment the vaccine is a cancer vaccine.

4 Claims, 9 Drawing Sheets

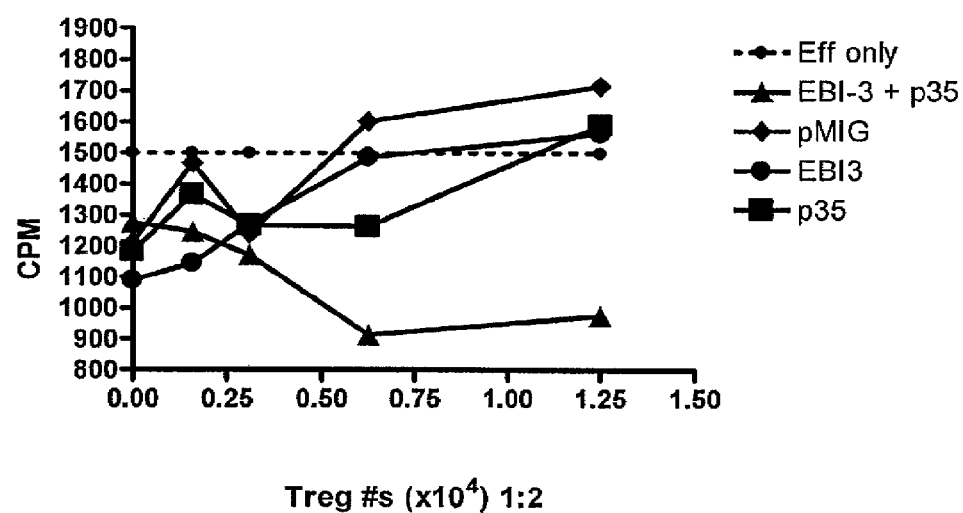

METHOD OF INHIBITING REGULATORY T-CELL ACTIVITY BY ADMINISTERING AN ANTIBODY THAT INHIBITS INTERLEUKIN 35

FEDERALLY SPONSORED RESEARCH OR DEVELOPMENT

This invention was made with United States Government support under NIH R01 Grant A139480 awarded by the National Institute of Health. The United States Government has certain rights in the invention.

CROSS REFERENCE TO RELATED APPLICATIONS

This application is a U.S. National Stage Application based on PCT/US2007/079310, filed Sep. 24, 2007, which claims the benefit of U.S. Provisional Application No. 60/846,434, filed on Sep. 22, 2006, all of which are herein incorporated by reference in their entirety.

RECOGNITION OF RESEARCH FUNDING

This invention was supported by funds received from the American Lebanese Syrian Associated Charities (ALSAC).

FIELD OF THE INVENTION

The present invention relates to methods for regulating T cell function in a subject, particularly regulatory T cell activity.

BACKGROUND OF THE INVENTION

The Epstein-Barr virus-induced gene 3 (EBI3; IL27b) product is a novel soluble hematopoietin component related to the p40 subunit (IL12b) of Interleukin 12 (IL12). EBI3 is widely expressed in cells and accumulates in the endoplasmic reticulum and associates with the molecular chaperone calnexin. Besides promoting Th1 cytokine production, EBI3 plays a critical regulatory role in the induction of Th2-type immune responses and the development of Th2-mediated tissue inflammation in vivo, which may be mediated through the control of invariant natural killer (NK) T cell function.

Interleukin 12 was identified and purified from the cell culture media of Epstein-Barr virus (EBV)-transformed B lymphoblastoid cell lines. Interleukin 12 is a 70 kDa heterodimeric cytokine composed of two disulfide-linked glycoproteins, p40 and p35 (IL12a). Interleukin 12 is primarily produced by macrophages and other antigen-presenting cells. Interleukin 12 has pleiotropic effects in the development of Th1 responses in NK and T lymphocytes, including induction of interferon (INF)-γ production, proliferation, and enhancement of cytotoxic activity, and inhibits Th2 responses.

Multiple, complex and interconnecting mechanisms control discrimination between self and non-self, including the thymic deletion of autoreactive T cells and the induction of anergy in peripheral T cells. In addition to these passive mechanisms, active suppression of autoreactive responder T cells is mediated by regulatory or suppressor T cells. Regulatory T ($T_R$) cells are powerful inhibitors of T cell activation both in vivo and in vitro. Regulatory T cells inhibit autoimmunity and inflammation, maintain immunologic tolerance, and are involved in the induction of tumor antigen tolerance (for reviews, see, Shevach, E. M., *Nat. Rev. Immunol.* 2:389-400, 2002; Sakaguchi, S., *Ann. Rev. Immunol.* 22:531-562, 2004; and Mapara and Sykes, *J. Clin. Oncology* 22:1136-51, 2004).

A major factor limiting immune recognition of cancer cells is the fact that tumors arise from a subject's own tissue and therefore express mainly self antigens to which the subject's T cells have been tolerized, either centrally (i.e., in the thymus) or peripherally. This situation is manifested as tolerance of T cells that display a high avidity for the normal self antigens expressed by the tumor, leaving only functional T cells with low avidity. This problem is exemplified by p53. Because of its high level of expression in certain malignancies, wild-type p53 is a potential target antigen for immunotherapy in a broad spectrum of neoplastic diseases. However, because of low-level expression in normal tissues, T cell tolerance by clonal deletion of high-avidity T cells in the thymus is an obstacle to generating an effective immune response following vaccination with a wild-type p53 antigen (Theobald et al., *J. Exp. Med.* 185:833-41, 1997). Nevertheless, it is possible to detect and clonally expand T cells specific for tumor-associated antigens (TAA) from tumor-bearing subjects. However, even if TAA-specific cells are present at detectable levels in tumor-bearing subjects, they are often incompetent to reject the tumor (Lee et al., *Nat. Med.* 5:677-85, 1999).

A number of vaccination approaches are currently being evaluated in clinical trials in efforts to induce host immune responses against a variety of solid tumors (e.g., colon cancer, prostate cancer, melanoma, and renal cell carcinoma). These strategies are all based on the observation that tumors are often poor antigen presenting cells. The lack of costimulatory molecules on their surface and the failure to produce stimulatory cytokines may make them poorly immunogenic and sometimes even tolerogenic. The approaches investigated include the use of gene-modified tumor cells (Soiffer et al., *Proc. Natl. Acad. Sci. USA* 95:13141-46, 1998), the use of professional antigen presenting cells (e.g., dendritic cells) or dendritic cells fused to tumor cells (Gong et al., *Blood* 99:2512-17, 2002; Gong et al., *Nat. Med.* 3:558-61, 1997), and DNA transfer using naked DNA or viral vectors.

Vaccination with dendritic cells has led to systemic T cell responses in treated subjects. However, clinical responses have been less striking, although some patients showed significant antitumor responses, including some complete responses (Nestle et al., *Nat. Med.* 4:328-32, 1998; Tjoa et al., *Prostate* 40:125-29, 1999; Murphy et al., *Prostate* 39:54-59, 1999). Therefore, there remains a need for the development of effective therapies for enhancing antitumor immunity.

SUMMARY OF THE INVENTION

The present invention is directed to methods for inhibiting a regulatory T cell function in a subject. In one embodiment, methods of the invention include administering to the subject a therapeutically effective amount of an Interleukin 35 (IL35; previously designated Interleukin 34, IL34)-specific binding agent. Interleukin 35-specific binding agents include antibodies, such as monoclonal antibodies, or fragments thereof, modified polypeptides designed to interfere with IL35 formation or activity, or small molecule inhibitors, such as chemical compounds.

A method for treating a subject having a cancer with a cancer vaccine is also provided. The method includes (i) administering to the subject a therapeutically effective amount of an IL35-specific binding agent and (ii) administering to the subject a cancer vaccine, where the IL35-specific binding agent enhances the efficacy of the cancer vaccine. In specific, non-limiting examples, the IL35-specific binding agent includes an antibody, such as a monoclonal antibody, or fragments thereof, or a small molecule inhibitor, such as a chemical compound. In one embodiment, administration of the therapeutically effective amount of the IL35-specific binding agent and administration of the cancer vaccine is sequential, in any order. Alternatively, administration of the therapeutically effective amount of the IL35-specific binding agent and administration of the cancer vaccine is simultaneous.

Methods for enhancing the immunogenicity of a vaccine or overcoming a suppressed immune response to a vaccine in a subject are further provided. These methods include (i) administering to the subject a therapeutically effective amount of an IL35-specific binding agent and (ii) administering to the subject a vaccine, where the IL35-specific binding agent enhances the immunogenicity of the vaccine or overcomes the suppressed immune response to the vaccine. In specific, non-limiting examples, the IL35-specific binding agent includes an antibody, such as a monoclonal antibody, or fragments thereof, or a small molecule inhibitor, such as a chemical compound. In one embodiment, administration of the therapeutically effective amount of the IL35-specific binding agent and administration of the vaccine is sequential, in any order. Alternatively, administration of the therapeutically effective amount of the IL35-specific binding agent and administration of the vaccine is simultaneous.

BRIEF DESCRIPTION OF THE DRAWINGS

FIGS. 2A & 2B. RNA was extracted and cDNA generated. Quantitative real-time PCR analysis was performed using β-actin as an endogenous control. Relative mRNA expression was determined by the comparative CT method (*p=0.008, **p=0.06). Data represent the mean±SEM of 4 (FIG. 2A) and 2 (FIG. 2B) independent experiments. FIG. 2C. Sorted $T_E$ and $T_R$ cells ($3\times10^6$ cells/lane) were cultured for 36 hours in the absence of stimuli. Cells were lysed and supernatant collected for overnight IP with an anti-IL12a (p35) mAb, eluted proteins resolved on an SDS-PAGE gel and blotted with anti-EBI3 mAb. Two exposure times are shown. Data are representative of 2 independent experiments. FIG. 2D. Relative mRNA expression was determined from purified $T_E$ or $T_R$ cells under indicated conditions; unstimulated, stimulated for 48 hours with anti-CD3/CD28 or activated in culture containing both $T_E$ and $T_R$ cells. Data represent the mean±SEM of 2 independent experiments (*p=0.008). FIG. 2E. 6.5 (TCR transgenic-hemagglutinin specific) CD4$^+$ $T_E$ cells were purified by MACS and activated with anti-CD3/CD28 for 2 days. T cells were retrovirally transduced with vector alone or Foxp3. After resting, qPCR was performed as described herein. Data represent the mean±SEM of 2 independent experiments (*p=0.002, **p=0.02).

FIG. 3A. Splenic $T_E$ cells ($2.5\times10^4$) were incubated with irradiated splenocytes as antigen-presenting cells ($2.5\times10^4$) and $T_R$ cells as indicated in the presence of anti-CD3 mAb (2C11) for 60 hours, pulsed with [$^3$H]thymidine for 8 hours and cell proliferation measured. FIG. 3B. $T_E$ and $T_R$ cells were sorted from spleens and lymph nodes of wild-type (WT), EBI3$^{-/-}$ and IL12$^{-/-}$ mice. Sorted $T_R$ cells were mixed at different ratios with antigen-presenting cells, naïve wild-type $T_E$ cells ($2.5\times10^4$ cells/well) and 5 μM anti-CD3. Cells were cultured for 72 hours and pulsed with [$^3$H]-thymidine (1 μCi/well) for the last 8 hours of culture. Data represent mean±SEM of 5 (4 for IL12a$^{-/-}$ $T_R$) independent experiments (*p=0.0002, **p=0.008). FIG. 3C. Wild-type $T_E$ cells ($2\times10^6$) alone or with WT, EBI3$^{-/-}$ or IL12a$^{-/-}$ $T_R$ cells ($5\times10^5$) were injected intravenously into RAG1$^{-/-}$ mice. Seven days post-transfer the mice were sacrificed and splenic T cell numbers determined by flow cytometry. Data represent mean±SEM of 3 independent experiments with 8-12 mice per group (*p=0.002, **p=0.02).

FIG. 4A. Percent weight change following $T_R$ cell transfer. FIG. 4B. Colonic histology scores of experimental mice are shown. Data in both panels represent mean±SEM of 8-11 mice per group from 4 independent experiments (*p=0.02, **p=0.05).

FIG. 5A. Naïve splenic T cells were activated for 48 hours with anti-CD3 mAb prior to transduction with EBI3, p35 (IL12a), EBI3+p35 (IL35), or pMIG (vector control). Following transduction, cells were expanded for 6 days, rested for 2 days and sorted for equal expression of the constructs. The T cells were then tested for their ability (at indicated cell numbers) to suppress proliferation of $T_E$ cells activated with irradiated splenocytes as antigen-presenting cells ($2.5\times10^4$) and $T_R$ cells as indicated in the presence of anti-CD3 mAb. Effector T cells were allowed to proliferate for 60 hours, then were pulsed with [$^3$H]thymidine for 8 hours and cell proliferation measured. FIG. 5B. 6.5 (TCR transgenic-HA specific) CD4$^+$ $T_E$ cells were purified by MACS and activated with anti-CD3/CD28 for 2 days. T cells were retrovirally transduced, sorted and titrated into an in vitro $T_R$ assay with antigen-presenting cells, 10 μg/ml HA 110-120 peptide and naïve 6.5 CD4$^+$CD25$^-$ $T_E$ cells. Data represent mean±SEM of 3 independent experiments. FIG. 5C. HEK293T cells were transiently transfected with empty GFP encoding vector or vectors containing "native" or "single chain" IL35. Cells were sorted for equivalent GFP expression and cultured for 36 hours to facilitate protein secretion. Dialyzed, filtered supernatant from cells was mixed at indicated ratios with anti-CD3/CD28 coated sulfate latex beads and $T_E$ cells in a proliferation assay. Data represent mean±SEM of 4 independent experiments.

DETAILED DESCRIPTION OF THE INVENTION

Figure 1:
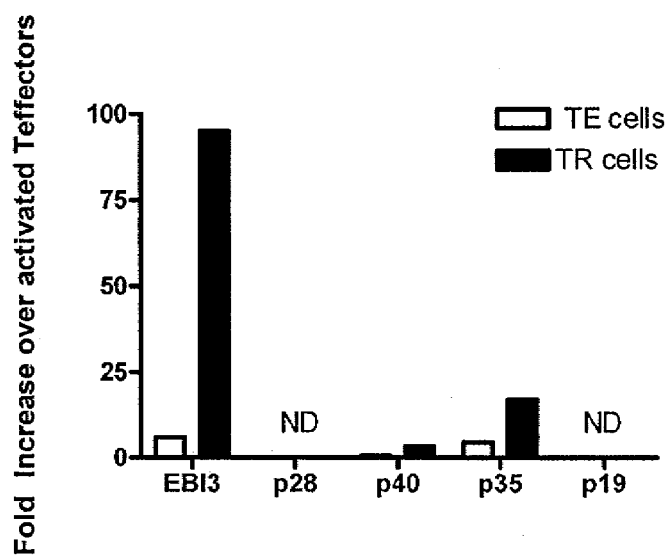
FIG. 1 illustrates that EBI3 and p35 (IL12a) are highly expressed by $T_R$ cells. Real-time RT-PCR analysis of IL12-related genes was performed on T cells sorted from C57BL/6 mice. Data presented as relative mRNA expression.

Compositions and methods for modulating T cell function in a subject are provided. The compositions comprise antagonists that are specific for IL35, or the IL35 subunits EBI3 and p35 (IL12a), but do not recognize other cytokines or cytokine combinations (e.g., an IL35-specific binding agent). In particular, the antagonists of the invention do not recognize or bind IL12, IL27, and the like. By "specific binding agent" is intended an agent that binds substantially only to a defined target. Thus an IL35-specific binding agent binds substantially only to a subunit (i.e., EBI3 or p35) of the heterodimeric glycoprotein or to the heterodimer itself, or inhibits IL35 activity. Likewise, an IL35 receptor (IL35R)-specific binding agent binds substantially only the IL35 receptor. As IL35 shares subunits with IL12 (p35) and IL27 (EBI3), an IL35-specific binding agent that binds substantially only to IL35 but not to IL12 or IL27 is preferred. Specific binding agents include, but are not limited to, antibodies, proteins that are designed to interfere with IL35 binding, formation or activity, proteins that compete with binding of a subunit (i.e., EBI3 or p35) to its complement subunit, proteins that bind IL35, and small molecules. A binding agent specifically binds if it binds only to EBI3, p35, or IL35, or fragments and closely related variants that share at least 80%, at least 90%, at least 95% or greater sequence identity to EBI3, p35, or IL35.

For purposes of the present invention, percent sequence identity is determined using the Smith-Waterman homology search algorithm using an affine gap search with a gap open penalty of 12 and a gap extension penalty of 2, BLOSUM matrix of 62. The Smith-Waterman homology search algorithm is taught in Smith and Waterman (*Adv. Appl. Math.* 2:482-489, 1981). A variant may, for example, differ from the reference protein by as few as 1 to 15 amino acid residues, as few as 1 to 10 amino acid residues, such as 6-10, as few as 5, as few as 4, 3, 2, or even 1 amino acid residue.

By "proteins that compete with binding of a subunit" is intended a protein that is designed to compete with binding of a subunit (i.e., EBI3 or p35) to its complement subunit. In this manner, EBI3 and p35 modified proteins can be made that are capable of binding to the complement subunit but that result in a defective IL35 molecule. By "modified EBI3 or p35 protein" is intended an amino acid sequence for EBI3 or p35 that has been modified by amino acid substitutions, deletions, additions and the like. That is, the resulting IL35 molecule does not retain the immunoregulatory activity. In this manner, mutations can be introduced into the EBI35 or p35 amino acid sequences and the resulting proteins tested for their abilities to bind their complement subunit. Such modified proteins can be made recombinantly, by proteolytic digestion, by chemical synthesis, etc. Internal or terminal fragments of a polypeptide can be generated by removing one or more nucleotides from one end or both ends of a nucleic acid which encodes the polypeptide. Mutations can be made in the corresponding nucleic acid sequence encoding the EBI35 or p35 polypeptide and expression of the mutagenized DNA produces modified polypeptide fragments or proteins.

EBI3 and p35 are known in the art. The human EBI3 gene encodes a protein of about 33 kDa. The protein shares about 27% sequence identity to the p40 subunit of human IL12. Nucleic acid and amino acid sequences for EBI3 are known. See, for example, SEQ ID NOs:1 and 2 of WO97/13859 (human) and GenBank Accession Numbers NM015766 and BC046112 (mouse). Nucleic acid and amino acid sequences for p35 are also known in the art and include SEQ ID NOs:3 and 4 of WO97/13859 (human) and GenBank Accession Numbers NM_000882 and M86672 (mouse).

Interleukin 35 refers to any intramolecular complex or single molecule comprising at least one EBI3 polypeptide component and at least one p35 polypeptide component. Typically, in vivo, EBI3 and p35 associate via non-covalent association. For purposes of the present invention, the EBI3-p35 components may be associated with one another either covalently or non-covalently for the purpose of raising specific antibodies. In some examples, EBI3 and p35 can be coexpressed as a fusion protein.

By "small molecule inhibitor" is intended a molecule of a size comparable to those molecules generally used in pharmaceuticals. The term excludes biological macromolecules (e.g., proteins, nucleic acids, etc.). Preferred small organic molecules range in size up to about 5000 Da, more preferably up to 2000 Da, and most preferably up to about 1000 Da.

Small molecule inhibitors can disrupt protein-protein interactions between a protein (both membrane bound and soluble) and its receptor, such as between the IL35 heterodimer and its receptor. The preparation of small molecule inhibitors is well known in the art. For example, although protein-protein interactions occur over a large surface area, X-ray crystallography and site-directed mutagenesis can be used to map the compact, centralized regions of protein-protein interfaces, often termed "hot spots," that are crucial for the interaction.

Non-limiting examples of small molecule inhibitors include chemical compounds, inorganic molecules, organic molecules, organic molecules containing an inorganic component, molecules including a radioactive atom, synthetic molecules, and peptidomimetics (e.g., short, peptide fragments that mimic the most common peptide motifs, such as an α-helix or β-sheet). As a specific binding agent, small molecule inhibitors may be more permeable to cells, less susceptible to degradation, and less apt to elicit an undesired immune response than large molecules.

The present invention further provides methods for inhibiting a regulatory T cell function in a subject. $T_R$ cells, also known as suppressor T cells, downregulate immune responses for both foreign and self antigens. Regulatory T cells have immunoregulatory properties and are actively involved in maintaining immune tolerance (i.e., in preventing autoimmunity), but also control various immune reactions (Chatila, T. A., *J. Allergy Clin. Immunol.* 116:949-59, 2005; Bluestone and Tang, *Curr. Opin. Immunol.* 17:638-42, 2005; and Schwartz, R. H., *Nat. Immunol.* 6:327-30, 2005). One class of $T_R$ cells, $CD4^+CD25^+$ suppressor T cells, is characterized by the expression of CD4 and CD25 (the Interleukin 2 receptor α-chain). These cells are often referred to as "natural regulatory T cells" (Bluestone and Abbas, *Nat. Rev. Immunol.* 3:253-57, 2003) or "innate regulatory T cells" (Cortez et al., *Transplantation* 77:S12-15, 2004), and are produced by the thymus as a functionally distinct subpopulation of T cells. Their development critically depends on expression of the forkhead transcription factor Foxp3 (Hori and Sakaguchi, *Microbes Infect.* 6:745-51, 2004). $CD4^+Foxp3^+$ $T_R$ cells are powerful inhibitors of T cell activation both in vivo and in vitro.

Other classes of regulatory T cells with diverse phenotypes and antigen specificities have been described (Maggi et al., *Autoimmun. Rev.* 4:579-586, 2005 and Levings and Roncarolo, *Curr. Topics Micro. Immunol.* 293:303-26, 2005). For example, "adaptive regulatory T cells," which are also referred to as "acquired regulatory T cells," are a population of antigen-induced regulatory T cells induced in the periphery after encounter with pathogens and foreign antigens (Cortez et al., *Transplantation* 77:S12-15, 2004; Mills and McGuirk, *Seminars Immunol.* 16:107-17, 2004; and Vigouroux et al., *Blood* 104:26-33, 2004).

By "inhibiting a regulatory T cell function in a subject" is intended reducing and/or blocking of one or more of the suppressive effects mediated by $T_R$ cells. While not being bound by any theory, it is believed that $T_R$ cells mediate their suppressive effects through both cell contact-dependent mechanisms (involving their T cell receptors and/or other cell surface-expressed molecules), and cytokine-dependent mechanisms (including, e.g., IL10 and TGF-β). In one embodiment, reducing and/or blocking of one or more of the suppressive effects mediated by $T_R$ cells is achieved by inhibiting the activation and/or proliferation of $T_R$ cells. The inhibition of the activation and/or proliferation of $T_R$ cells can be measured relative to a control population of cells, such as responder or effector T cells. For purposes of the invention, $T_R$ cell function is reduced at least 30%, at least 50%, at least 60%, at least 70%, at least 80%, or at least 90% as compared to control cells, such as responder T cells.

As used herein, "responder T cells" or "effector T cells" refers to a subpopulation of mature T cells that facilitate an immune response through cell activation and/or the secretion of cytokines. In one embodiment, the responder T cells are $CD4^+CD25^-$ T cells. In another embodiment, the responder T cells are $CD8^+CD25^-$ T cells. One example of a responder T cell is a T lymphocyte that proliferates upon stimulation by an antigen, such as a tumor antigen. Another example of a responder T cell is a T lymphocyte whose responsiveness to stimulation can be suppressed by $T_R$ cells.

Production of Anti-IL35 Antibodies

As noted herein, the invention includes antibodies specifically reactive with IL35, EBI3 or p35. Antibodies, including monoclonal antibodies (mAbs) can be made by standard protocols. See, for example, Harlow and Lane, *Using Antibodies: A Laboratory Manual*, CSHL, New York, 1999. Briefly, a mammal such as a mouse, hamster or rabbit can be immunized with an immunogenic form of a peptide. Techniques for conferring immunogenicity on a protein or peptide include conjugation to carriers or other techniques, well known in the art. In preferred embodiments, the subject antibodies are immunospecific for antigenic determinants of EBI3, p35, or IL35. See, SEQ ID NOs:1-4 of WO97/13859 for the human nucleic acid and amino acid sequences for EBI3 and p35, respectively, and GenBank Accession Numbers NM015766, BC046112, NM_000882, and M86672 for the mouse nucleic acid and amino acid sequences for EBI3 and p35, respectively.

The antibodies of the invention include antibodies that specifically bind IL35, EBI3 and p35. As discussed herein, these antibodies are collectively referred to as "anti-IL35 antibodies". Thus, by "anti-IL35 antibodies" is intended antibodies specific for IL35, antibodies specific for EBI3 and antibodies specific for p35. All of these antibodies are encompassed by the discussion herein. The respective antibodies can be used alone or in combination in the methods of the invention.

By "antibodies that specifically bind" is intended that the antibodies will not substantially cross react with another polypeptide. By "not substantially cross react" is intended that the antibody or fragment has a binding affinity for a non-homologous protein which is less than 10%, more preferably less than 5%, and even more preferably less than 1%, of the binding affinity for EBI3, p35, or IL35.

The anti-IL35 antibodies disclosed herein and for use in the methods of the present invention can be produced using any antibody production method known to those of skill in the art. Thus, polyclonal sera may be prepared by conventional methods. In general, a solution containing the IL35, EBI3 or p35 antigen is first used to immunize a suitable animal, preferably a mouse, rat, rabbit, or goat. Rabbits or goats are preferred for the preparation of polyclonal sera due to the volume of serum obtainable, and the availability of labeled anti-rabbit and anti-goat antibodies.

Polyclonal sera can be prepared in a transgenic animal, preferably a mouse bearing human immunoglobulin loci. In a preferred embodiment, Sf9 (*Spodoptera frugiperda*) cells expressing IL35, EBI3 or p35 are used as the immunogen. Immunization can also be performed by mixing or emulsifying the antigen-containing solution in saline, preferably in an adjuvant such as Freund's complete adjuvant, and injecting the mixture or emulsion parenterally (generally subcutaneously or intramuscularly). A dose of 50-200 µg/injection is typically sufficient. Immunization is generally boosted 2-6 weeks later with one or more injections of the protein in saline, preferably using Freund's incomplete adjuvant. One may alternatively generate antibodies by in vitro immunization using methods known in the art, which for the purposes of this invention is considered equivalent to in vivo immunization. Polyclonal antisera are obtained by bleeding the immunized animal into a glass or plastic container, incubating the blood at 25° C. for one hour, followed by incubating at 4° C. for 2-18 hours. The serum is recovered by centrifugation (e.g., 1,000×g for 10 minutes). About 20-50 ml per bleed may be obtained from rabbits.

Production of the Sf9 cells is disclosed in U.S. Pat. No. 6,004,552. Briefly, sequences encoding human IL35, EBI3 or p35 are recombined into a baculovirus using transfer vectors. The plasmids are co-transfected with wild-type baculovirus DNA into Sf9 cells. Recombinant baculovirus-infected Sf9 cells are identified and clonally purified. Recombinant baculovirus-infected Sf9 cells are identified and clonally purified.

Preferably the antibody is monoclonal in nature. By "monoclonal antibody" is intended an antibody obtained from a population of substantially homogeneous antibodies, that is, the individual antibodies comprising the population are identical except for possible naturally occurring mutations that may be present in minor amounts. The term is not limited regarding the species or source of the antibody. The term encompasses whole immunoglobulins as well as fragments such as Fab, F(ab')2, Fv, and others which retain the antigen binding function of the antibody. Monoclonal antibodies are highly specific, being directed against a single antigenic site on the target polypeptide. Furthermore, in contrast to conventional (polyclonal) antibody preparations that typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler and Milstein (*Nature* 256: 495-97, 1975), or may be made by recombinant DNA methods (see, e.g., U.S. Pat. No. 4,816,567). The "monoclonal antibodies" may also be isolated from phage antibody libraries using the techniques described in, for example, Clackson et al. (*Nature* 352:624-28, 1991), Marks et al. (*J. Mol. Biol.* 222:581-97, 1991) and U.S. Pat. No. 5,514,548.

By "epitope" is intended the part of an antigenic molecule to which an antibody is produced and to which the antibody will bind. Epitopes can comprise linear amino acid residues (i.e., residues within the epitope are arranged sequentially one after another in a linear fashion), nonlinear amino acid residues (referred to herein as "nonlinear epitopes"—these epitopes are not arranged sequentially), or both linear and nonlinear amino acid residues.

As discussed herein, mAbs can be prepared using the method of Kohler and Milstein, or a modification thereof. Typically, a mouse is immunized with a solution containing an antigen. Immunization can be performed by mixing or emulsifying the antigen-containing solution in saline, preferably in an adjuvant such as Freund's complete adjuvant, and injecting the mixture or emulsion parenterally. Any method of immunization known in the art may be used to obtain the monoclonal antibodies of the invention. After immunization of the animal, the spleen (and optionally, several large lymph nodes) are removed and dissociated into single cells. The spleen cells may be screened by applying a cell suspension to a plate or well coated with the antigen of interest. The B cells expressing membrane bound immunoglobulin specific for the antigen bind to the plate and are not rinsed away. Resulting B cells, or all dissociated spleen cells, are then induced to fuse with myeloma cells to form hybridomas, and are cultured in a selective medium. The resulting cells are plated by serial dilution and are assayed for the production of antibodies that specifically bind the antigen of interest (and that do not bind to unrelated antigens). The selected mAb-secreting hybridomas are then cultured either in vitro (e.g., in tissue culture bottles or hollow fiber reactors), or in vivo (as ascites in mice).

Where the anti-IL35 antibodies of the invention are to be prepared using recombinant DNA methods, the DNA encoding the monoclonal antibodies is readily isolated and sequenced using conventional procedures (e.g., by using oligonucleotide probes that are capable of binding specifically to genes encoding the heavy and light chains of murine antibodies). The hybridoma cells described herein serve as a preferred source of such DNA. Once isolated, the DNA can be placed into expression vectors, which are then transfected into host cells such as E. coli cells, simian COS cells, Chinese Hamster Ovary (CHO) cells, or myeloma cells that do not otherwise produce immunoglobulin protein, to obtain the synthesis of monoclonal antibodies in the recombinant host cells. Review articles on recombinant expression in bacteria of DNA encoding an antibody includes Skerra, A. (Curr. Opinion in Immunol. 5:256-62, 1993) and Phickthun, A. (Immunol. Revs. 130:151-88, 1992). Alternatively, antibody can be produced in a cell line such as a CHO cell line, as disclosed in U.S. Pat. Nos. 5,545,403; 5,545,405 and 5,998,144. Briefly the cell line is transfected with vectors capable of expressing a light chain and a heavy chain, respectively. By transfecting the two proteins on separate vectors, chimeric antibodies can be produced. Another advantage is the correct glycosylation of the antibody.

Additionally, the term "anti-IL35 antibody" as used herein encompasses chimeric and humanized anti-IL35 antibodies. By "chimeric" antibodies is intended antibodies that are most preferably derived using recombinant deoxyribonucleic acid techniques and which comprise both human (including immunologically "related" species, e.g., chimpanzee) and non-human components. Thus, the constant region of the chimeric antibody is most preferably substantially identical to the constant region of a natural human antibody; the variable region of the chimeric antibody is most preferably derived from a non-human source and has the desired antigenic specificity to the IL35 antigen. The non-human source can be any vertebrate source that can be used to generate antibodies to a human IL35 antigen or material comprising a human IL35 antigen. Such non-human sources include, but are not limited to, rodents (e.g., rabbit, rat, mouse, etc.; see, e.g., U.S. Pat. No. 4,816,567) and non-human primates (e.g., Old World Monkeys, Apes, etc.; see, e.g., U.S. Pat. Nos. 5,750,105 and 5,756,096). As used herein, the phrase "immunologically active" when used in reference to chimeric/humanized anti-IL35 antibodies means chimeric/humanized antibodies that bind human IL35.

By "humanized" is intended forms of anti-IL35 antibodies that contain minimal sequence derived from non-human immunoglobulin sequences. For the most part, humanized antibodies are human immunoglobulins (recipient antibody) in which residues from a hypervariable region (also known as complementarity determining region or CDR) of the recipient are replaced by residues from a hypervariable region of a non-human species (donor antibody) such as mouse, rat, rabbit, or nonhuman primate having the desired specificity, affinity, and capacity. The phrase "complementarity determining region" refers to amino acid sequences which together define the binding affinity and specificity of the natural Fv region of a native immunoglobulin binding site. See, for example, Chothia et al. (J. Mol. Biol. 196:901-17, 1987) and Kabat et al. (U.S. Dept. of Health and Human Services, NIH Publication No. 91-3242, 1991). The phrase "constant region" refers to the portion of the antibody molecule that confers effector functions.

Humanization can be essentially performed following the methods described by Jones et al. (Nature 321:522-25, 1986), Riechmann et al. (Nature 332:323-27, 1988) and Verhoeyen et al. (Science 239:1534-36, 1988), by substituting rodent or mutant rodent CDRs or CDR sequences for the corresponding sequences of a human antibody. See also U.S. Pat. Nos. 5,225,539; 5,585,089; 5,693,761; 5,693,762; and 5,859,205. In some instances, residues within the framework regions of one or more variable regions of the human immunoglobulin are replaced by corresponding non-human residues (see, for example, U.S. Pat. Nos. 5,585,089; 5,693,761; 5,693,762; and 6,180,370). Furthermore, humanized antibodies may comprise residues that are not found in the recipient antibody or in the donor antibody. These modifications are made to further refine antibody performance (e.g., to obtain desired affinity). In general, the humanized antibody will comprise substantially all of at least one, and typically two, variable domains, in which all or substantially all of the hypervariable regions correspond to those of a non-human immunoglobulin and all or substantially all of the framework regions are those of a human immunoglobulin sequence. The humanized antibody optionally also will comprise at least a portion of an immunoglobulin constant region (Fc), typically that of a human immunoglobulin. Accordingly, such "humanized" antibodies may include antibodies wherein substantially less than an intact human variable domain has been substituted by the corresponding sequence from a non-human species.

Also encompassed by the term "anti-IL35 antibodies" are xenogeneic or modified anti-IL35 antibodies produced in a non-human mammalian host, more particularly a transgenic mouse, characterized by inactivated endogenous immunoglobulin loci. In such transgenic animals, competent endogenous genes for the expression of light and heavy subunits of host immunoglobulins are rendered non-functional and substituted with the analogous human immunoglobulin loci. These transgenic animals produce human antibodies in the substantial absence of light or heavy host immunoglobulin subunits. See, for example, U.S. Pat. Nos. 5,877,397 and 5,939,598. Preferably, fully human antibodies to IL35 can be obtained by immunizing transgenic mice. One such mouse is disclosed in U.S. Pat. Nos. 6,075,181; 6,091,001; and 6,114,598.

Fragments of the anti-IL35 antibodies are suitable for use in the methods of the invention so long as they retain the desired affinity of the full-length antibody. Thus, a fragment of an anti-IL35 antibody will retain the ability to bind to IL35, EBI3 or p35. Such fragments are characterized by properties similar to the corresponding full-length anti-IL35 antibody; that is, the fragments will specifically bind IL35, EBI3 or p35. Such fragments are referred to herein as "antigen-binding" fragments.

Suitable antigen-binding fragments of an antibody comprise a portion of a full-length antibody, generally the antigen-binding or variable region thereof. Examples of antibody fragments include, but are not limited to, Fab, F(ab')$_2$, and Fv fragments and single-chain antibody molecules. By "Fab" is intended a monovalent antigen-binding fragment of an immunoglobulin that is composed of the light chain and part of the heavy chain. By F(ab')$_2$ is intended a bivalent antigen-binding fragment of an immunoglobulin that contains both light chains and part of both heavy chains. By "single-chain Fv" or "sFv" antibody fragments is intended fragments comprising the $V_H$ and $V_L$ domains of an antibody, wherein these domains are present in a single polypeptide chain. See, for example, U.S. Pat. Nos. 4,946,778; 5,260,203; 5,455,030; and 5,856,456. Generally, the Fv polypeptide further comprises a polypeptide linker between the $V_H$ and $V_L$ domains that enables the sFv to form the desired structure for antigen binding. For a review of sFv see Pluckthun, A. (1994) in *The Pharmacology of Monoclonal Antibodies*, Vol. 113, ed. Rosenburg and Moore (Springer-Verlag, New York), pp. 269-315.

Antibodies or antibody fragments can be isolated from antibody phage libraries generated using the techniques described in, for example, McCafferty et al. (*Nature* 348:552-54, 1990) and U.S. Pat. No. 5,514,548. Clackson et al. (*Nature* 352:624-28, 1991) and Marks et al. (*J. Mol. Biol.* 222:581-97, 1991) describe the isolation of murine and human antibodies, respectively, using phage libraries. Subsequent publications describe the production of high affinity (nM range) human antibodies by chain shuffling (Marks et al., *Bio/Technology* 10:779-83, 1992), as well as combinatorial infection and in vivo recombination as a strategy for constructing very large phage libraries (Waterhouse et al., *Nucleic. Acids Res.* 21:2265-66, 1993). Thus, these techniques are viable alternatives to traditional monoclonal antibody hybridoma techniques for isolation of monoclonal antibodies.

Various techniques have been developed for the production of antibody fragments. Traditionally, these fragments were derived via proteolytic digestion of intact antibodies (see, e.g., Morimoto et al., *J. Biochem. Biophys. Methods* 24:107-17, 1992 and Brennan et al., *Science* 229:81-3, 1985). However, these fragments can now be produced directly by recombinant host cells. For example, the antibody fragments can be isolated from the antibody phage libraries discussed above. Alternatively, Fab fragments can be directly recovered from *E. coli* and chemically coupled to form $F(ab')_2$ fragments (Carter et al., *Bio/Technology* 10:163-67, 1992). According to another approach, $F(ab')_2$ fragments can be isolated directly from recombinant host cell culture. Other techniques for the production of antibody fragments will be apparent to the skilled practitioner.

A representative assay to detect anti-IL35 antibodies specific to the IL35, EBI3 or p35-antigenic epitopes identified herein is a "competitive binding assay." Competitive binding assays are serological assays in which unknowns are detected and quantitated by their ability to inhibit the binding of a labeled known ligand to its specific antibody. Antibodies employed in such immunoassays may be labeled or unlabeled. Unlabeled antibodies may be employed in agglutination; labeled antibodies may be employed in a wide variety of assays, employing a wide variety of labels. Detection of the formation of an antibody-antigen complex between an anti-IL35 antibody and an epitope of interest can be facilitated by attaching a detectable substance to the antibody. Suitable detection means include the use of labels such as radionuclides, enzymes, coenzymes, fluorescers, chemiluminescers, chromogens, enzyme substrates or co-factors, enzyme inhibitors, prosthetic group complexes, free radicals, particles, dyes, and the like. Such labeled reagents may be used in a variety of well-known assays, such as radioimmunoassays, enzyme immunoassays, e.g., ELISA, fluorescent immunoassays, and the like. See, for example, U.S. Pat. Nos. 3,766,162; 3,791,932; 3,817,837; and 4,233,402.

Small Molecule Screening

The likelihood of an assay identifying an agent that acts as an IL35 small molecule inhibitor is increased when the number and types of test agents used in the screening system is increased. Recently, attention has focused on the use of combinatorial chemical libraries to assist in the generation of new small molecule inhibitor leads. A combinatorial chemical library is a collection of diverse chemical compounds generated by either chemical synthesis or biological synthesis by combining a number of chemical "building blocks." For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks (see, e.g., Gallop et al., 37:1233-50, 1994).

Preparation and screening of combinatorial chemical libraries is well known to those of skill in the art. Such combinatorial chemical libraries include, for example, peptide libraries (see, e.g., U.S. Pat. No. 5,010,175). Peptide synthesis is by no means the only approach envisioned and intended for use with the present invention. Other chemistries for generating chemical diversity libraries can also be used. Such chemistries include: peptoids (see, e.g., WO 91/19735), encoded peptides (see, e.g., WO 93/20242), random bio-oligomers (see, e.g., WO 92/00091), benzodiazepines (see, e.g., U.S. Pat. No. 5,288,514), diversomers such as hydantoins, benzodiazepines and dipeptides (see, e.g., Hobbs et al., *Proc. Nat. Acad. Sci. USA* 90:6909-13, 1993), vinylogous polypeptides (see, e.g., Hagihara et al., *J. Amer. Chem. Soc.* 114:6568-70, 1992), nonpeptidal peptidomimetics with a β-D-Glucose scaffolding (see, e.g., Hirschmann et al., *J. Amer. Chem. Soc.* 114:9217-18, 1992), analogous organic syntheses of small compound libraries (see, e.g., Chen et al., *J. Amer. Chem. Soc.* 116:2661-62, 1994), oligocarbamates (see, e.g., Cho et al., Science 261:1303-05, 1993), and peptidyl phosphonates (see, e.g., Campbell et al., *J. Org. Chem.* 59:658-60, 1994). In addition, a number of combinatorial libraries are commercially available, as is well known to one of skill in the art.

High throughput techniques are used when screening any of the various libraries described herein. As is well known to one of skill in the art, a number of high throughput screening systems are commercially available (e.g., Zymark Corp., Hopkinton, Mass.; Air Technical Industries, Mentor, Ohio; Beckman Instruments, Inc., Fullerton, Calif.; and Precision Systems, Inc., Natick, Mass.). These systems typically automate entire procedures including all sample and reagent pipetting, liquid dispensing, timed incubations, and final readings of the microplate in detector(s) appropriate for the assay. These configurable systems provide high throughput and rapid start up as well as a high degree of flexibility and customization.

Methods of Therapy using the Compositions of the Invention

As disclosed herein, methods of the invention are directed to the use of specific binding agents for inhibiting $T_R$ cell function. Thus, the compositions are useful for inhibiting T cell function in a subject. EBI3 and p35 pair to form a novel cytokine, IL35, with immunosuppressive activity. Interleukin 35 is secreted by CD4$^+$Foxp3$^+$ $T_R$ cells, and may be secreted by other cells (such as subpopulations of CD8$^+$ T cells, γδ T cells and NK T cells that have regulatory function). It exhibits immunoregulatory activity and is required for maximal $T_R$ cell function. The ability to specifically inhibit IL35 can be used to reduce or block regulatory T cell function. Inhibition may be by antibodies, modified proteins or small molecules that specifically block binding to its receptor or disrupt IL35 chain pairing. As IL35 shares homology in some regions with IL12 and IL27, the inhibitory molecules of the invention (i.e., IL35-specific antagonists or IL35-specific binding agents) are designed to recognize and interact with IL35 or its subunits but not IL12 or IL27.

The compositions find use in boosting the efficacy of vaccines. Since, $T_R$ cells are involved in the induction of tumor antigen tolerance (Mapara and Sykes, *J. Clin. Oncology* 22:1136-51, 2004), the compositions are useful for increasing the efficacy of anti-cancer vaccines. Reducing $T_R$ cell function can also be beneficial for vaccines that are poorly immunogenic; therefore, the compositions can be used with any vaccine including vaccines for diphtheria, tetanus, pertussis, polio, measles, mumps, rubella, hepatitis B, *Haemophilus influenzae* type b, varicella, meningitis, human immunodeficiency virus, tuberculosis, Epstein Barr virus, malaria, hepatitis E, dengue, rotavirus, herpes, human papillomavirus, and cancers In one embodiment, inhibition of a $T_R$ cell function in a subject includes administering to the subject a therapeutically effective amount of an IL35-specific binding agent. Administration can begin whenever inhibition of a $T_R$ cell function in a subject is desired, for example to prevent or overcome induction of tumor antigen tolerance by $T_R$ cells in a subject.

As used herein, "a therapeutically effective amount" of an IL35-specific binding agent is an amount which, when administered to a subject, is sufficient to achieve a desired effect, such as inhibiting a $T_R$ cell function, in a subject being treated with that composition. For example, this can be the amount of an IL35-specific binding agent useful in preventing or overcoming induction of tumor antigen tolerance by $T_R$ cells in a subject, or the amount required to enhance the efficacy of a vaccine (e.g., a cancer vaccine) in a subject. Ideally, a therapeutically effective amount of an IL35-specific binding agent is an amount sufficient to prevent or overcome induction of tumor antigen tolerance by $T_R$ cells in a subject, or the amount required to enhance the efficacy of a vaccine (e.g., a cancer vaccine) in a subject, without causing a substantial cytotoxic effect in the subject. The effective amount of an IL35-specific binding agent useful for preventing or overcoming induction of tumor antigen tolerance by $T_R$ cells in a subject and/or enhancing the efficacy of a vaccine (e.g., a cancer vaccine) will depend on the subject being treated, the severity of the affliction, and the manner of administration of the IL35-specific binding agent.

In some embodiments a "therapeutically effective amount" or "effective amount" (for non-topical administration, such as oral administration, or intravenous or intraperitoneal injection) of a pharmaceutical composition containing an IL35-specific binding agent is from about 0.1 to about 200 mg/kg body weight in single or divided doses; for example from about 1 to about 100 mg/kg, from about 2 to about 50 mg/kg, from about 3 to about 25 mg/kg, or from about 5 to about 10 mg/kg. Acceptable dosages of the IL35-specific binding agent are, for example, dosages that achieve a target tissue concentration similar to that which produces the desired effect in vitro. Alternatively, therapeutically effective amounts of an IL35-specific binding agent can be determined by animal studies. When animal assays are used, a dosage is administered to provide a target tissue concentration similar to that which has been shown to be effective in the animal assays. It is recognized that the method of treatment may comprise a single administration of a therapeutically effective amount or multiple administrations of a therapeutically effective amount of the IL35-specific binding agents of the invention.

Any delivery system or treatment regimen that effectively achieves the desired effect of inhibiting a $T_R$ cell function can be used. Accordingly, pharmaceutical compositions including an IL35-specific binding agent (such as an antibody and/or a small molecule inhibitor) are also described herein. The IL35-specific binding agent is present in the composition in a therapeutically effective amount.

Formulations for pharmaceutical compositions are well known in the art. For example, *Remington's Pharmaceutical Sciences* (18$^{th}$ ed.; Mack Publishing Company, Eaton, Pa., 1990), describes compositions and formulations suitable for pharmaceutical delivery of one or more IL35-specific binding agents, such as one or more anti-IL35 antibodies and/or small molecule inhibitors combined with various pharmaceutically acceptable additives, as well as a dispersion base or vehicle. Desired additives include, but are not limited to, pH control agents, such as arginine, sodium hydroxide, glycine, hydrochloric acid, citric acid, and the like. In addition, local anesthetics (e.g., benzyl alcohol), isotonizing agents (e.g., sodium chloride, mannitol, sorbitol), adsorption inhibitors (e.g., Tween 80), solubility enhancing agents (e.g., cyclodextrins and derivatives thereof), stabilizers (e.g., serum albumin), reducing agents (e.g., glutathione), and preservatives (e.g., antimicrobials, and antioxidants) can be included.

Therapeutically effective amounts of an IL35-specific binding agent, such as an antibody and/or a small molecule inhibitor, for use in the present invention can be administered by any route, including parenteral administration, for example, intravenous, intraperitoneal, intramuscular, intraperitoneal, intrasternal, or intraarticular injection, or infusion, or by sublingual, oral, topical, intranasal, or transmucosal administration, or by pulmonary inhalation. The pharmaceutical compositions of the present invention can be administered at about the same dose throughout a treatment period, in an escalating dose regimen, or in a loading-dose regime (for example, in which the loading dose is about two to five times the maintenance dose). In some embodiments, the dose is varied during the course of a treatment based on the condition of the subject being treated, the apparent response to the therapy, and/or other factors as judged by one of ordinary skill in the art. In some embodiments long-term treatment with a disclosed pharmaceutical composition is contemplated.

In a specific embodiment, it may be desirable to administer a therapeutically effective amount of an IL35-specific binding agent, such as an antibody and/or a small molecule inhibitor, locally to an area in need of treatment (e.g., to an area of the body where inhibiting a $T_R$ cell function is desired). This can be achieved by, for example, local or regional infusion or perfusion during surgery, topical application, injection, catheter, suppository, or implant (for example, implants formed from porous, non-porous, or gelatinous materials, including membranes, such as sialastic membranes or fibers), and the like. In one embodiment, administration can be by direct injection at the site (or former site) of a cancer that is to be treated. In another embodiment, the therapeutically effective amount of an IL35-specific binding agent is delivered in a vesicle, such as liposomes (see, e.g., Langer, *Science* 249: 1527-33, 1990 and Treat et al., in *Liposomes in the Therapy of Infectious Disease and Cancer*, Lopez Berestein and Fidler (eds.), Liss, N.Y., pp. 353-65, 1989).

In yet another embodiment, the therapeutically effective amount of an IL35-specific binding agent, such as an antibody and/or a small molecule inhibitor, can be delivered in a controlled release system. In one example, a pump can be used (see, e.g., Langer, *Science* 249:1527-33, 1990; Sefton, *Crit. Rev. Biomed. Eng.* 14:201-40, 1987; Buchwald et al., *Surgery* 88:507-16, 1980; Saudek et al., *N. Engl. J. Med.* 321:574-79, 1989). In another example, polymeric materials can be used (see, e.g., Levy et al., *Science* 228:190-92, 1985; During et al., *Ann. Neurol.* 25:351-56, 1989; Howard et al., *J. Neurosurg.* 71:105-12, 1989). Other controlled release systems, such as those discussed by Langer (*Science* 249:1527-33, 1990), can also be used.

Also provided by the present invention are methods for enhancing the efficacy or immunogenicity of a vaccine in a subject, or overcoming a suppressed immune response to a vaccine in a subject, including (i) administering to the subject a therapeutically effective amount of an IL35-specific binding agent and (ii) administering to the subject a vaccine. In one embodiment, the vaccine is a cancer vaccine. In a specific example, the method further includes administering to the subject at least one additional therapeutic agent, such as a cytokine, a glucocorticoid, an anthracycline (e.g., doxorubicin or epirubicin), a fluoroquinolone (e.g., ciprofloxacin), an antifolate (e.g., methotrexate), an antimetabolite (e.g., fluorouracil), a topoisomerase inhibitor (e.g., camptothecin, irinotecan or etoposide), an alkylating agent (e.g., cyclophosphamide, ifosfamide, mitolactol, or melphalan), an antiandrogen (e.g., flutamide), an antiestrogen (e.g., tamoxifen), a platinum compound (e.g., cisplatin), a vinca alkaloid (e.g., vinorelbine, vinblastine or vindesine), or mitotic inhibitor (e.g., paclitaxel or docetaxel). In some embodiments of the present invention, the amount of the vaccine (and/or the additional therapeutic agent) administered to the subject in the presence of the IL35-specific binding agent is lower than when the vaccine (and/or the additional therapeutic agent) is administered alone.

By "vaccine" is intended a composition useful for stimulating a specific immune response (or immunogenic response) in a subject. In some embodiments, the immunogenic response is protective or provides protective immunity. For example, in the case of a disease-causing organism the vaccine enables the subject to better resist infection with or disease progression from the organism against which the vaccine is directed. Alternatively, in the case of a cancer, the vaccine strengthens the subject's natural defenses against cancers that have already developed. These types of vaccines may also prevent the further growth of existing cancers, prevent the recurrence of treated cancers, and/or eliminate cancer cells not killed by prior treatments. Without being bound by theory, it is believed that an immunogenic response arises from the generation of neutralizing antibodies, T helper cells, or cytotoxic cells of the immune system, or all of the above.

By "enhancing the efficacy" or "enhancing the immunogenicity" with regard to a vaccine is intended improving an outcome, for example, as measured by a change in a specific value, such as an increase or a decrease in a particular parameter of an activity of a vaccine associated with protective immunity. In one embodiment, enhancement refers to at least a 25%, 50%, 100% or greater than 100% increase in a particular parameter. In another embodiment, enhancement refers to at least a 25%, 50%, 100% or greater than 100% decrease in a particular parameter. In one example, enhancement of the efficacy/immunogenicity of a vaccine refers to an increase in the ability of the vaccine to inhibit or treat disease progression, such as at least a 25%, 50%, 100%, or greater than 100% increase in the effectiveness of the vaccine for that purpose. In a further example, enhancement of the efficacy/immunogenicity of a vaccine refers to an increase in the ability of the vaccine to recruit the subject's natural defenses against cancers that have already developed, such as at least a 25%, 50%, 100%, or greater than 100% increase in the effectiveness of the vaccine for that purpose.

Similarly, by "overcoming a suppressed immune response" with regard to a vaccine is intended improving an outcome, for example, as measured by a change in a specific value, such as a return to a formerly positive value in a particular parameter of an activity of a vaccine associated with protective immunity. In one embodiment, overcoming refers to at least a 25%, 50%, 100% or greater than 100% increase in a particular parameter. In one example, overcoming a suppressed immune response to a vaccine refers to a renewed ability of the vaccine to inhibit or treat disease progression, such as at least a 25%, 50%, 100%, or greater than 100% renewal in the effectiveness of the vaccine for that purpose. In a further example, overcoming a suppressed immune response to a vaccine refers to a renewed ability of the vaccine to recruit the subject's natural defenses against cancers that have already developed, such as at least a 25%, 50%, 100%, or greater than 100% renewal in the effectiveness of the vaccine for that purpose.

As disclosed herein, the present invention provides methods for enhancing the efficacy or immunogenicity of a vaccine in a subject, or overcoming a suppressed immune response to a vaccine in a subject. Representative vaccines include, but are not limited to, vaccines against diphtheria, tetanus, pertussis, polio, measles, mumps, rubella, hepatitis B, *Haemophilus influenzae* type b, varicella, meningitis, human immunodeficiency virus, tuberculosis, Epstein Barr virus, malaria, hepatitis E, dengue, rotavirus, herpes, human papillomavirus, and cancers.

Vaccines of interest include the two vaccines that have been licensed by the U.S. Food and Drug Administration to prevent virus infections that can lead to cancer: the hepatitis B vaccine, which prevents infection with the hepatitis B virus, an infectious agent associated with liver cancer (*MMWR Morb. Mortal. Wkly. Rep.* 46:107-09, 1997); and Gardasil™, which prevents infection with the two types of human papillomavirus that together cause 70 percent of cervical cancer cases worldwide (Speck and Tyring, *Skin Therapy Lett.* 11:1-3, 2006). Other treatment vaccines of interest include therapeutic vaccines for the treatment of cervical cancer, follicular B cell non-Hodgkin's lymphoma, kidney cancer, cutaneous melanoma, ocular melanoma, prostate cancer, and multiple myeloma.

The compositions of the invention can be coordinated with treatment with other cancer therapies besides vaccines including chemotherapy, anti-cancer antibody therapy, small molecule-based cancer therapy, and vaccine/immunotherapy-based cancer therapy, and combinations thereof. The compositions of the invention are generally used prior to treatment with a vaccine; however, they can be used either prior to, during, or after treatment of the subject with the other cancer therapy or, in the case of multiple combination therapies, either prior to, during, or after treatment of the subject with the other cancer therapies.

As will be understood by one of skill in the art, the methods disclosed herein for enhancing the efficacy or immunogenicity of a cancer vaccine in a subject will be relevant for various types of cancer vaccines, including, but not limited to, antigen/adjuvant vaccines (i.e., one or more cancer cell antigens combined with an adjuvant), whole cell tumor vaccines (either autologous or allogenic), dendritic cell vaccines (i.e., isolated dendritic cells that are stimulated with the subject's own cancer antigens and re-injected into the subject), and viral vectors and DNA vaccines (which use the nucleic acid sequence of a tumor antigen to produce a cancer antigen protein).

The immunosuppressive effects of $T_R$ cells (as well as the inhibition those effects) can be evaluated using many methods well known in the art. In one embodiment, a white blood cell count (WBC) is used to determine the responsiveness of a subject's immune system. A WBC measures the number of white blood cells in a subject. Using methods well known in the art, the white blood cells in a subject's blood sample are separated from other blood cells and counted. Normal values of white blood cells are about 4,500 to about 10,000 white blood cells/µl. Lower numbers of white blood cells can be indicative of a state of immunosuppression in the subject. In another embodiment, immunosuppression in a subject can be determined by way of a T lymphocyte count. T lymphocytes are differentiated from other white blood cells using standard methods in the art, such as, for example, immunofluorescence or fluorescence activated cell sorting (FACS). Reduced numbers of T cells, or a specific population of T cells (for example, $CD8^+$ T cells) can be used as a measurement of immunosuppression. A reduction in the number of T cells, or in a specific population of T cells, compared to the number of T cells (or the number of cells in the specific population) prior to a specific event can be used to indicate that immunosuppression has been induced.

Methods for the isolation and quantitation of $T_R$ cells, such as $CD4^+Foxp3^+$ $T_R$ cells, and other populations of T cells (e.g., $CD8^+$ cells), are well known in the art. Typically, labeled antibodies specifically directed to one or more cell surface markers are used to identify and quantify the T-cell population. The antibodies can be conjugated to other compounds including, but not limited to, enzymes, magnetic beads, colloidal magnetic beads, haptens, fluorochromes, metal compounds, radioactive compounds or drugs. The enzymes that can be conjugated to the antibodies include, but are not limited to, alkaline phosphatase, peroxidase, urease, and β-galactosidase. The fluorochromes that can be conjugated to the antibodies include, but are not limited to, fluorescein isothiocyanate (FITC), tetramethylrhodamine isothiocyanate, phycoerythrin (PE), allophycocyanins, and Texas Red. For additional fluorochromes that can be conjugated to antibodies see Haugland, R. P., *Handbook of Fluorescent Probes and Research Products*, published by Molecular Probes, $9^{th}$ Edition (2002). The metal compounds that can be conjugated to the antibodies include, but are not limited to, ferritin, colloidal gold, and particularly, colloidal superparamagnetic beads. The haptens that can be conjugated to the antibodies include, but are not limited to, biotin, digoxigenin, oxazalone, and nitrophenol. The radioactive compounds that can be conjugated or incorporated into the antibodies are known to the art, and include, but are not limited to, technetium 99 ($^{99}Tc$), $^{125}I$, and amino acids comprising any radionuclides, including, but not limited to, $^{14}C$, $^3H$ and $^{35}S$.

Fluorescence activated cell sorting can be used to sort cells that are $CD4^+$, $CD25^+$, both $CD4^+$ and $CD25^+$, or $CD8^+$ by contacting the cells with an appropriately labeled antibody. However, other techniques of differing efficacy may be employed to purify and isolate desired populations of cells. The separation techniques employed should maximize the retention of viability of the fraction of the cells to be collected. The particular technique employed will, of course, depend upon the efficiency of separation, cytotoxicity of the method, the ease and speed of separation, and what equipment and/or technical skill is required.

Additional separation procedures may include magnetic separation, using antibody-coated magnetic beads, affinity chromatography, cytotoxic agents, either joined to a monoclonal antibody or used in conjunction with complement, and "panning," which utilizes a monoclonal antibody attached to a solid matrix, or another convenient technique. Antibodies attached to magnetic beads and other solid matrices, such as agarose beads, polystyrene beads, hollow fiber membranes and plastic Petri dishes, allow for direct separation. Cells that are bound by the antibody can be removed from the cell suspension by simply physically separating the solid support from the cell suspension. The exact conditions and duration of incubation of the cells with the solid phase-linked antibodies will depend upon several factors specific to the system employed. The selection of appropriate conditions, however, is well known in the art.

Unbound cells then can be eluted or washed away with physiologic buffer after sufficient time has been allowed for the cells expressing a marker of interest (e.g., CD4 and/or CD25) to bind to the solid-phase linked antibodies. The bound cells are then separated from the solid phase by any appropriate method, depending mainly upon the nature of the solid phase and the antibody employed, and quantified using methods well known in the art. In one example, bound cells separated from the solid phase are quantified by FACS. Antibodies may be conjugated to biotin, which then can be removed with avidin or streptavidin bound to a support, or fluorochromes, which can be used with FACS to enable cell separation and quantitation, as known in the art.

As used herein, the singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. The subject matter of the present disclosure is further illustrated by the following non-limiting examples.

EXPERIMENTAL

Example 1

Isolation of Interleukin 35 a Regulatory T Cell-Specific Cytokine

Figure 2:
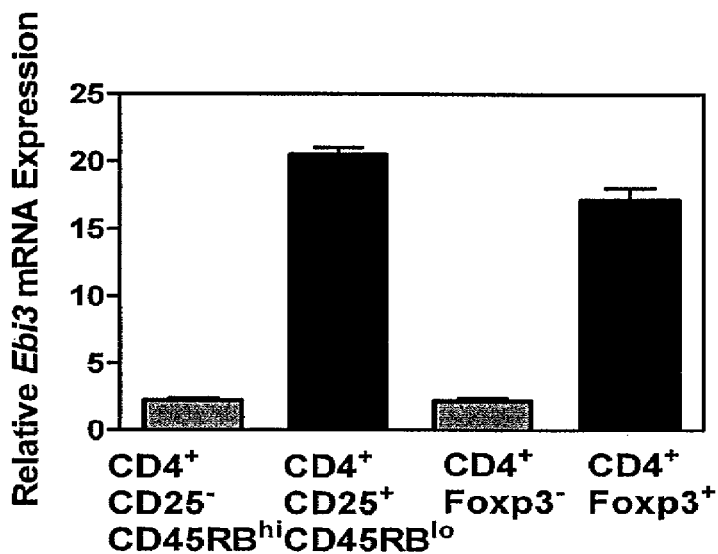
FIGS. 2A-E illustrate $T_R$-restricted expression of EBI3 and IL12a. Effector T ($T_E$) or $T_R$ cells from the spleens and lymph nodes of C57BL/6, Foxp3$^{gfp}$ or EBI3$^{-/-}$ mice were purified by FACS as indicated.
Figure 2:
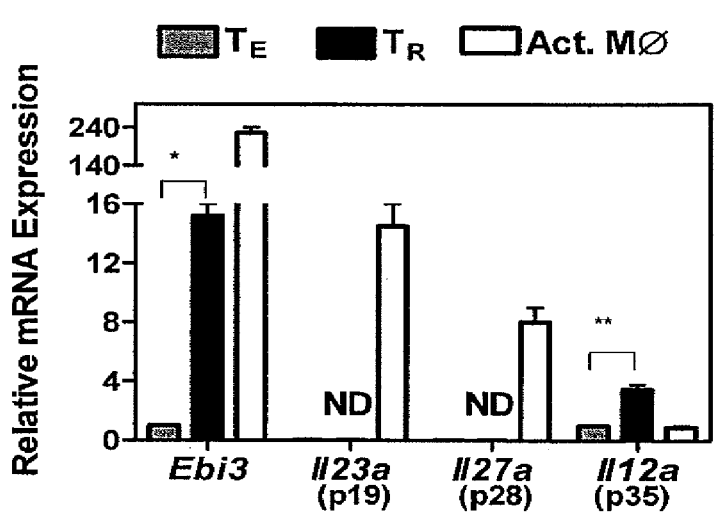
Figure 2:
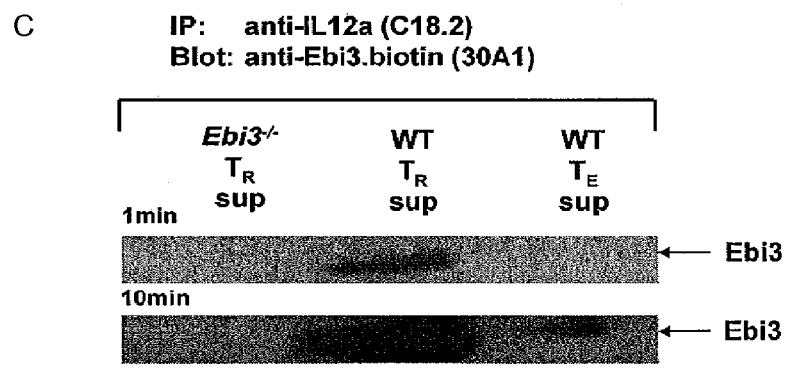
Figure 2:
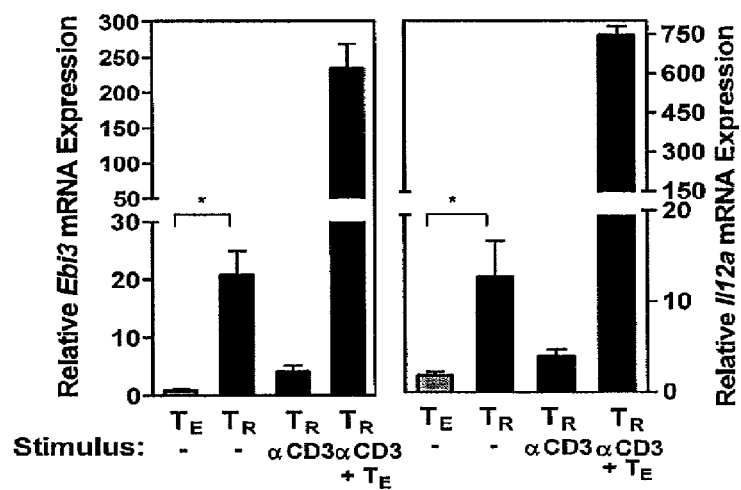
Figure 2:
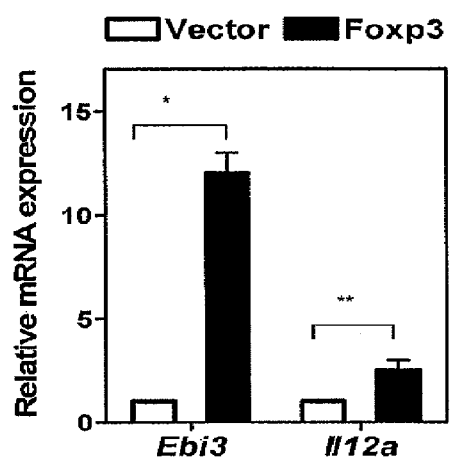

An Affymetrix gene analysis was performed for the purpose of identifying genes that are preferentially upregulated in or on $T_R$ cells. This analysis identified EBI3 as one of those genes. To verify the gene analysis data, quantitative real-time PCR (qPCR) was used to measure EBI3 mRNA expression. PCR results confirmed the upregulation of EBI3 expression in $T_R$ cells versus $T_E$ cells (FIG. 1). Confirmation of $T_R$-restricted expression of EBI3 was obtained by additional qPCR analysis of peripheral $CD4^+CD45RB^{lo}CD25^+$ $T_R$ cells versus naïve $CD4^+CD45RB^{hi}CD25^-$ $T_E$ cells (the standard phenotypic definition for $T_R$ and $T_E$ cells) purified from C57BL/6 mice, and $Foxp3^+$ $T_R$ cells versus $Foxp3^-$ $T_E$ cells sorted from $Foxp3^{gfp}$ knockin mice (Fontenot et al., *Immunity* 22:329-41, 2005), which express a GFP-Foxp3 chimeric protein (FIG. 2A). Literature suggests that neither α or β chains will be secreted alone, but rather, need to pair within the cell to be secreted. Interleukin 27 is a heterodimer of EBI3 and p28, whereas p40 can pair with p19 to yield IL23, or with p35 to yield IL12. Therefore, the expression of p40, EBI3, p35 (IL12a), p28, and p19 in $T_E$ cells and $T_R$ cells was measured via qPCR to determine putative binding partners for EBI3 in $T_R$ cells. PCR results demonstrated that p35 was the only IL12 family α chain expressed in $T_R$ cells (FIG. 2B). See also, Devergne et al., *Proc. Natl. Acad. Sci. USA* 94:12041-46, 1997.

The expression of intracellular EBI3 was assessed by flow cytometry in resting $T_R$ cells. Using three different EBI3-specific mAbs, resting wild-type $T_R$ cells, but not wild-type $T_E$ or EBI3$^{-/-}$ $T_R$ cells, were shown to express intracellular EBI3. Finally, immunoblot analysis clearly revealed the coimmunoprecipitation of EBI3 with IL12a in supernatants from resting $T_R$, but not $T_E$ cells or EBI3$^{-/-}$ $T_R$ cells (FIG. 2C). Taken together, these data demonstrate the preferential secretion of a novel EBI3/IL12a heterodimeric cytokine by $T_R$ cells amongst CD4$^+$ T cell populations.

Given that $T_R$ cells require activation through their TCR in order to exert their suppressive activity (Thornton et al., *J. Exp. Med.* 188:287-96, 1998; Thornton et al., *J. Immunol.* 164:183-90, 2000; Takahashi et al., *Int. Immunol.* 10:1969-80, 1998), an assessment of how EBI3 and IL12a mRNA levels were altered following $T_R$ cell activation in the absence or presence of $T_E$ cells was made. Both EBI3 and IL12a mRNA were significantly reduced following anti-CD3 stimulation, but dramatically upregulated (234- and 740-fold, respectively) in $T_R$ cells recovered from an in vitro $T_R$ assay, and thus in the process of active suppression (FIG. 2D). Indeed, the increase in IL12a mRNA far exceeded that observed in activated macrophages. These data demonstrate that a novel EBI3/IL12a heterodimeric cytokine is produced by $T_R$ cells, which is potentiated during active suppression of $T_E$ cells.

The discrete, differential expression of EBI3 in $T_R$ versus $T_E$ cells suggests that its expression may be controlled by transcriptional processes that regulate $T_R$ development and function. Indeed, EBI3 expression was concordant with Foxp3, which is required for $T_R$ development (Zheng et al., *Nat. Immunol.* 8:457-62, 2007). EBI3 mRNA was present in CD4$^+$Foxp3$^+$ thymocytes but essentially absent in CD4$^+$CD8$^+$ and CD4$^+$Foxp3$^-$ thymocytes. To determine if EBI3 is a downstream target of Foxp3, purified $T_E$ cells were transduced with retroviral vectors encoding Foxp3 plus GFP or GFP alone. Foxp3-transduced $T_E$ cells exhibited considerably elevated EBI3 transcript levels compared with the GFP alone controls, while Foxp3 induced limited expression of IL12a mRNA (FIG. 2E). These data provide a mechanistic basis for the restricted secretion of the EBI3/IL12a heterodimer by $T_R$ cells, with EBI3 being a downstream target of Foxp3.

Example 2

Interleukin 35 is Required for Optimal $T_R$ Cell Function

Neither EBI3$^{-/-}$ nor IL12a$^{-/-}$ mice have any overt autoimmunity or inflammatory disease (Boirivant et al., *J. Exp. Med.* 188:1929-39, 1998; Mattner et al., *Eur. J. Immunol.* 26:1553-59, 1996). Indeed, the percentage of $T_R$ cells in these mice and their Foxp3 expression is comparable to wild-type mice. This raises the possibility that the consequence of lacking a negative regulatory EBI3/IL12a cytokine may be negated by the lack of the proinflammatory cytokines IL27 and IL12 in the EBI3$^{-/-}$ and IL12a$^{-/-}$ mice, respectively. Indeed, when challenged, EBI3$^{-/-}$ mice are more susceptible to leishmaniasis (Zahn et al., *Eur. J. Immunol.* 35:1106-12, 2005). Likewise, IL12a$^{-/-}$, distinct from IL12b$^{-/-}$ (p40) mice, are more susceptible to *Helicobacter*-induced colitis (Kullberg et al., *J. Exp. Med.* 203:2485-94, 2006), *Leishmania major* infection (Mattner et al., *Eur. J. Immunol.* 26:1553-59, 1996), experimental autoimmune encephalomyelitis (Gran et al., *J. Immunol.* 169:7104-10, 2002; Becher et al., *J. Clin. Invest.* 110: 493-97, 2002), and collagen-induced arthritis (Murphy et al., *J. Exp. Med.* 198:1951-57, 2003).

Figure 3:
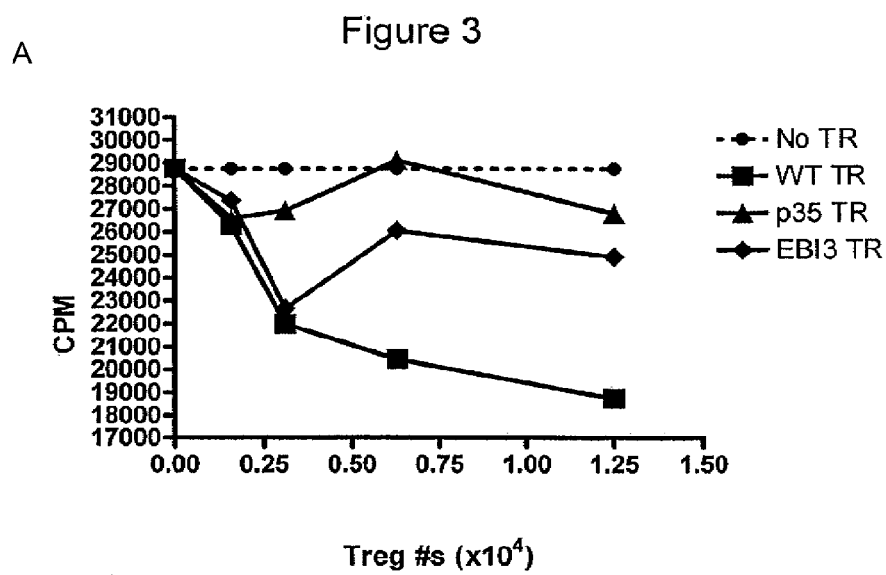
FIG. 3A-C demonstrate that EBI3 and p35 (IL12a) are required for optimal $T_R$ cell function.
Figure 3:
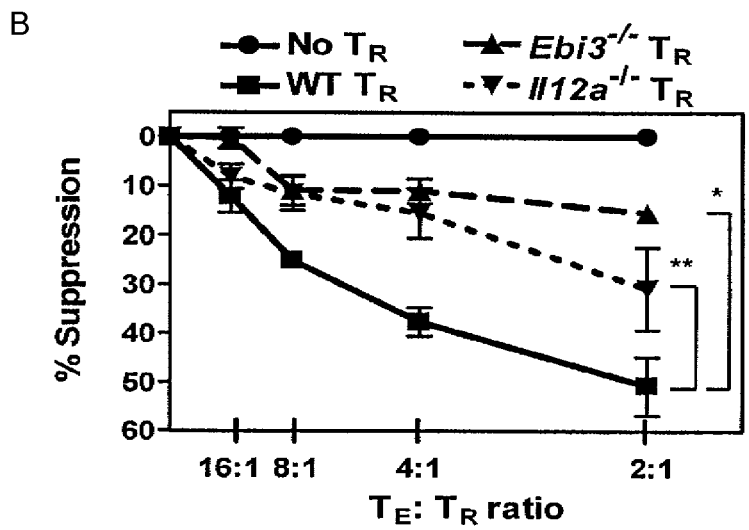
Figure 3:
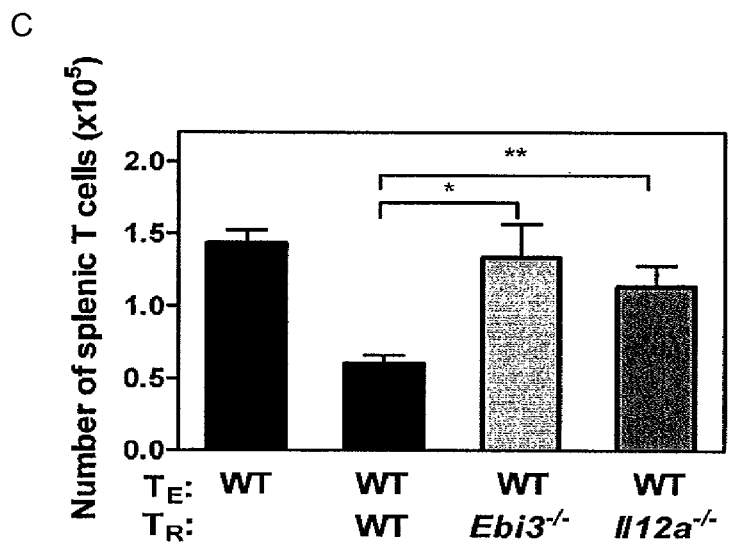

To determine whether the loss of EBI3 or IL12a expression would have functional implications for $T_R$ cells, $T_E$ cells and $T_R$ cells were isolated from wild-type, EBI3$^{-/-}$ and IL12a$^{-/-}$ mice (Boirivant et al., *J. Exp. Med.* 188:1929-39, 1998; Mattner et al., *Eur. J. Immunol.* 26:1553-59, 1996). An in vitro $T_R$ cell assay was performed to determine whether $T_R$ cells lacking EBI3 or IL12a could suppress $T_E$ cell proliferation. Wild-type $T_R$ cells could suppress proliferation of $T_E$ cells in a dose dependent manner. In contrast, both EBI3$^{-/-}$ and IL12a$^{-/-}$ $T_R$ cells were less capable of suppressing $T_E$ cell proliferation, showing that EBI3 and IL12a are required for optimal $T_R$ cell function (FIGS. 3A & 3B).

To determine EBI3$^{-/-}$ and IL12a$^{-/-}$ $T_R$ cell function in vivo, their ability to control the homeostatic expansion of $T_E$ cells was evaluated. In vivo, $T_R$ cells have been shown to control the homeostatic expansion of $T_E$ cells in a lymphopenic, RAG1$^{-/-}$ environment (Annacker et al., *Immunol. Rev.* 182:5-17, 2001; Annacker et al., *J. Immunol.* 164:3573-80, 2000; Workman et al., *J. Immunol.* 174:688-95, 2004). Therefore, to determine whether the expression of EBI3 and IL12a influenced the ability of $T_R$ cells to control homeostatic expansion, purified wild-type $T_E$ cells either alone, or in the presence of wild-type, EBI3$^{-/-}$ or IL12a$^{-/-}$ $T_R$ cells, were adoptively transferred into RAG1$^{-/-}$ mice. As RAG1$^{-/-}$ mice lack T and B cells, expansion of adoptively transferred T cells represent the only T cell population present in these mice. Splenic T cell numbers were determined 7-10 days post-transfer. In the presence of wild-type $T_R$ cells, $T_E$ cell expansion was significantly reduced, while minimal reduction in wild-type $T_E$ cell expansion was observed in the presence of either EBI3$^{-/-}$ or IL12a$^{-/-}$ $T_R$ cells (FIG. 3C).

$T_R$ cells have also been shown to control colitis in mice, resembling IBD, that is initiated experimentally by transferring naïve T cells into RAG1$^{-/-}$ recipients (Izcue et al., *Immunol. Rev.* 212:256-71, 2006). In these experiments, severity of disease is monitored clinically, by weight loss, and histologically, utilizing a semi-quantitative grading scheme to score pathology. Recovery from disease, marked by weight gain and decreased histopathology, is observed only in mice that receive purified $T_R$ cells approximately four weeks after the initial $T_E$ cell transfer (Mottet et al., *J. Immunol.* 170:3939-43, 2003).

Figure 4:
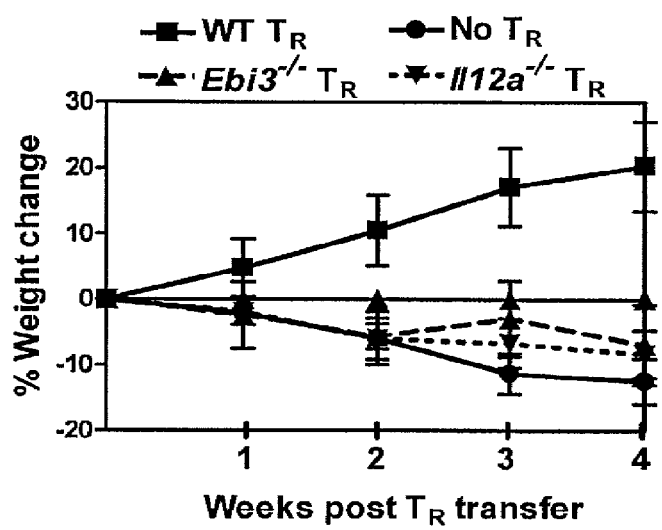
FIGS. 4A-B illustrate that EBI3$^{-/-}$ $T_R$ cells fail to treat inflammatory bowel disease (IBD). RAG1$^{-/-}$ mice received CD4$^+$CD25$^-$CD45RB$^{hi}$ $T_E$ cells via the tail vein. After 3-4 weeks, mice developed clinical symptoms of IBD and were given a second transfer of wild-type or EBI3$^{-/-}$ $T_R$ cells.
Figure 4:
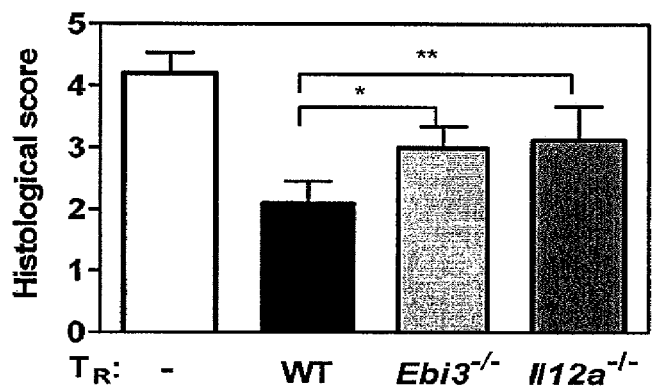

This recovery model of IBD was chosen to test the functionality of EBI3$^{-/-}$ and IL12a$^{-/-}$ $T_R$ cells in vivo. After wild-type $T_E$-recipient RAG1$^{-/-}$ mice developed clinical symptoms of IBD (approximately 4 weeks), they received wild-type, EBI3$^{-/-}$ or IL12a$^{-/-}$ $T_R$ cells and were monitored daily. Wild-type $T_R$-recipient mice were noticeably healthier within 5-7 days, had restored appetite, and resumed weight gain (FIG. 4A). However, EBI3$^{-/-}$ and IL12a$^{-/-}$ $T_R$ recipients continued to lose weight, with some mice dying within the first 10 days post-$T_R$ cell transfer. After 4 weeks (8 weeks after initial $T_E$ cell transfer), histological analysis was performed to assess the extent of recovery. Severe IBD pathology including loss of goblet cells and mucus secretion, mucosal hyperplasia, extensive ulceration, marked transmural lymphohistiocytic inflammation, extensive infiltration of CD3$^+$ T cells, and effacement of the normal architecture by the inflammatory infiltrate was observed in the non-$T_R$ recipients. In wild-type $T_R$ recipients, there was substantial reduction of the mean pathology score, significantly reduced inflammation, reduced CD3$^+$ T cell infiltration, and regeneration of goblet cells, and mucus secretion. In contrast, EBI3$^{-/-}$ and IL12a$^{-/-}$ $T_R$ recipients had only an approximately 50% reduction in the pathology score, as defined by goblet cell destruction, mucosal hyperplasia and cellular infiltration (FIG. 4B). Thus, the slightly improved histological score was insufficient to mediate weight gain and recovery from colitis. Similarly, EBI3$^{-/-}$ and IL12a$^{-/-}$ T$_R$ were unable to reduce colitis and weight loss to the same extent as wild type T$_R$ cells in a traditional co-transfer model of IBD. These results demonstrate that EBI3 and IL12a are required by T$_R$ cells for maximal regulatory activity in vitro and in vivo.

Example 3

Both EBI3 and IL12a are Required for the Generation of Interleukin 35

Figure 5:
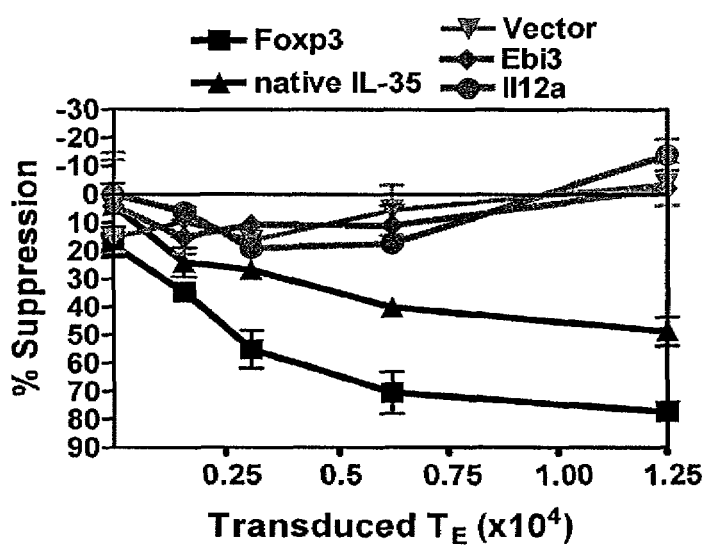
FIGS. 5A-C demonstrate that ectopic expression of IL35 and recombinant IL35 suppress $T_E$ cell proliferation.
Figure 5:
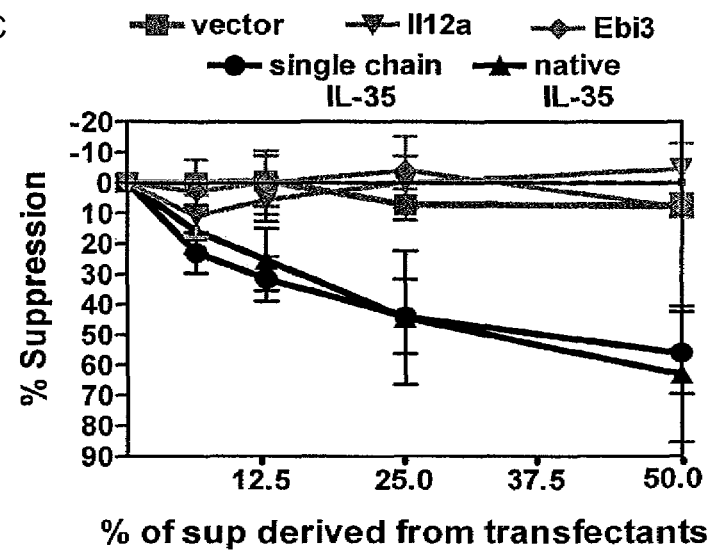

Several studies have shown that ectopic expression of Foxp3 or the regulatory protein LAG-3 can confer regulatory activity on naïve T$_E$ cells (Hori and Sakaguchi, *Science* 299: 1057-61, 2003; Fontenot et al., *Nat. Immunol.* 4:330-36, 2003; Huang et al., *Immunity* 21:503-13, 2004). As the qPCR data indicated that EBI3+IL12a is a functional heterodimer important to T$_R$ cell function, EBI3+IL12a was ectopically expressed to see if its expression could confer regulatory activity to non-regulatory T cells. Naïve T$_E$ cells from hemagglutinin-specific clone 6.5 TCR transgenic mice were transduced with EBI3, IL12a, EBI3+IL12a, or vector alone to assess the impact of expressing these proteins on cellular function. With ectopic expression of EBI3+IL12a, but not with either protein alone, transduced T$_E$ cells gained T$_R$ cell function as measured by their ability to inhibit proliferation of naïve T cells (FIG. 5A). Recombinant IL35 derived from 3T3 cells or 293T cells also inhibited T cell proliferation. The observation that non-regulatory T cells gain regulatory activity by the expression of EBI3+IL12a, but not independently, demonstrates that both EBI30 and IL12a are required for the generation of this regulatory cytokine.

Purified T$_E$ cells from the clone 6.5 TCR transgenic mice were also transduced with retroviral vectors encoding the expression of GFP alone, or GFP plus either Foxp3, EBI3, IL12a or "native" IL35 (i.e., EBI3-2A-IL12a -stoichiometric, bicistronic expression of EBI3 and IL12a in a single vector; Szymczak-Workman et al. in *Gene Transfer: Delivery and Expression*, Friedmann and Rossi (eds.), Cold Spring Harbor Laboratory Press, N.Y., pp. 137-47, 2006; Szymczak and Vignali, *Exp. Opin. Biol. Ther.* 5:627-38, 2005; Holst et al., *Nature Methods* 3:191-97, 2006). T cell transductants were sorted for GFP equivalency and co-cultured with naïve, wild-type T$_E$ cells in an antigen-driven proliferation assay to determine if these proteins bestowed regulatory potential. The results confirmed that T cells expressing IL35, but not either chain alone, suppressed T$_E$ cell proliferation in a titratable fashion, to a level that was approximately two thirds of the regulatory activity observed with the Foxp3-transduced T cells (FIG. 5B).

Given that IL35 is secreted by T$_R$ cells and forced expression confers regulatory activity on an otherwise non-regulatory T cell, an assessment was made as to whether recombinant IL35 could directly inhibit T$_E$ cell proliferation. HEK293T cells (human embryonic kidney) were transfected with plasmids encoding expression of either "native" IL35 (EBI3-2A-IL12a ) or "single chain" IL35 (i.e., EBI3 and IL12a expressed as a single chain protein; Hisada et al., *Cancer Res.* 64:1152-56, 2004). Empty vector, EBI3 alone and IL12a alone controls were also generated. Recombinant IL35 was then assessed to determine if it could suppress the proliferation of T$_E$ cells stimulated with anti-CD3/CD28-coated microbeads. Media containing either form of recombinant IL35, but not any of the three controls, potently suppressed T$_E$ cell proliferation in a titratable fashion (FIG. 5C). Co-culture with irradiated HEK293T cell transfectants gave identical results. These data demonstrate that soluble, recombinant IL35 alone is sufficient to suppress T cell proliferation.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed:

1. A method of inhibiting a regulatory T-cell function in a subject, comprising administering to a subject in need of inhibiting a regulatory T-cell function a therapeutically effective amount of a specific binding agent, wherein said specific binding agent comprises an antibody that inhibits Interleukin 35 (IL35) activity, wherein the therapeutically effective amount of said antibody inhibits a regulatory T-cell function in said subject.

2. The method of claim 1, wherein said specific binding agent comprises an anti-IL35 antibody that specifically binds to the IL35 heterodimer.

3. The method of claim 1, wherein said specific binding agent comprises an antibody that binds to the EBI3 subunit of IL35.

4. The method of claim 1, wherein said specific binding agent comprises an antibody that binds to the p35 subunit of IL35.

* * * * *